United States Patent
Bombardelli et al.

(10) Patent No.: US 6,372,458 B1
(45) Date of Patent: Apr. 16, 2002

(54) PROCESS FOR THE BIOTRANSFORMATION OF COLCHICONE COMPOUNDS INTO THE CORRESPONDENCE 3-GLYCOSYL DERIVATIVES

(75) Inventors: Ezio Bombardelli; Cesare Ponzone, both of Milan (IT)

(73) Assignee: Indena S.p.A., Milan (IT)

( * ) Notice: Subject to any disclaimer, the term of this patent is extended or adjusted under 35 U.S.C. 154(b) by 0 days.

(21) Appl. No.: 09/539,867

(22) Filed: Mar. 31, 2000

Related U.S. Application Data

(63) Continuation-in-part of application No. PCT/EP98/06226, filed on Sep. 30, 1998.

(30) Foreign Application Priority Data

Oct. 3, 1997 (IT) .......................................... MI97A2255

(51) Int. Cl.⁷ ................................................. C12P 19/44
(52) U.S. Cl. ...................... 435/74; 435/132; 435/252.5; 435/147; 435/148; 435/170

(58) Field of Search ....................... 435/74, 170, 252.5, 435/132, 147, 148

(56) References Cited

U.S. PATENT DOCUMENTS 3,090,729 A * 5/1963 Bellet .......................... 435/74

OTHER PUBLICATIONS

Poulev et al., J. Ferment. Bioeng., vol. 79, 1, pp. 33–38, 1995.*

* cited by examiner

*Primary Examiner*—Irene Marx
(74) *Attorney, Agent, or Firm*—Pennie & Edmonds LLP

(57) ABSTRACT

The present invention relates to the microbial biotransformation of colchiconic compounds into derivative compounds, which are glycosylated exclusively at the C-3 position of the six-member ring. The process of the present invention provides the 3-O-glycosyl derivatives in high yields and purity.

18 Claims, No Drawings

PROCESS FOR THE BIOTRANSFORMATION OF COLCHICONE COMPOUNDS INTO THE CORRESPONDENCE 3-GLYCOSYL DERIVATIVES

CROSS-REFERENCE TO RELATED APPLICATION

This application is a continuation-in-part of the U.S. national phase of International Application No. PCT/EP98/06226 filed Sep. 30, 1998, the content of which is expressly incorporated herein by reference thereto.

FIELD OF THE INVENTION

The present invention relates to the microbial biotransformation of colchiconic compounds into derivative compounds, which are glycosylated exclusively at the C-3 position of the six-member ring. The process of the present invention provides the 3-O-glycosyl derivatives in high yields and purity.

BACKGROUND ART

A number of efforts using either chemical reactions or biotransformations have been made to obtain highly regiospecific glycosydated derivatives of compounds of formula (I), which is shown below, and related colchicinoid compounds.

For example, the chemical reaction route consists of sequences of complex, non-specific, non-selective reactions involving different molecular sites, which produce a mixture of glycosydated derivatives. Thus, the conversion yields of the desired effective or active product, which is specifically glycosydated at the C-3 position of the aromatic ring, are very low.

The biological approach substantially relates to the biotransformation of colchicinoid compounds such as colchicine and thiocolchicine, which are indirectly related with the colchicone compounds. For example, a known transformation, which is accomplished by a culture of *Centella asiatica*, yields derivatives, which are monoglycosydated at the C-2 and at C-3 positions of the aromatic ring (Solet, J. M., et al., Phytochemistry, 33, 4, 817–820, 1993). Thus, the transformation is not highly selective and also provides poor yields and productivity.

Other efforts to biotransform colchicinoid compounds have yielded simple demethylations of the methoxy groups bound to the aromatic ring at the C-2 and C-3 positions. These transformations are also characterized by limited yields, limited productivity, and by poor regioselectivity.

Attempts have been made to transform colchicine and its derivatives into the corresponding 3-demethylated derivatives using *Streptomyces griseus* and/or *Streptomyces spectabilis* (Hufford C. D. et al. J. Pharm. Sc., 68, 10, 1239–1242, 1979). Other workers have attempted the same biotransformation using different strains of Streptomyces and of other species of bacteria and fungi (Bellet P. et al. GB-923421, 1959). These results, however, confirm that these known microbial enzymes non-selectively produce the C-2, C-3, or C-10 derivatives of the alkaloid molecule. Moreover, the productivity of these catalytic systems are rather poor due to the low conversion yields, a requirement for reduced substrate concentrations, and frequent degradation of the tropolone ring.

More recently, Poulev et al. J. Ferment. Bioeng. 79, 1, 33–38, 1995 have obtained a specific demethylation using bacterial microorganisms, however, the demethylation also occurs with generally poor yields and productivity.

Enzymes from microorganisms similar to the above mentioned microorganisms, such as, for example, Streptomyces, Bacillus, have been applied to biotransform compounds, such as maytansinoids (U.S. Pat. No. 4,361,650 to Asai et al. and Izawa, M., et al., J. Antibiotics, 34, 12, 1587–1590, 1981). In these references, however, the catalyzed reaction consists exclusively of a demethylation characterized by low conversion yields and productivity.

Brumm, P. J., et al. (Starch, 43, 8, 319–323, 1991) have described the glycosyl transferase activity of an α-amylase enzyme, which was derived from strains of *Bacillus megaterium* and has particularly high acceptor specificities for glucose or glucosides. For example, starting from starch, cyclodextrin-glucosyl transferases, produced by the same microbial source, catalyze the α-1,4-transglucosylation of rubusoside (13-0-β-D-glucosyl-steviol β-D-glucosyl ester). It has been reported (Darise, M., et al., Agric. Bioel. Chem., 48, 10, 2483–2488, 1984), that, in this bioconversion, the acceptor of the transferase reaction is the substrate glucide fraction. Cyclodextrin-glycosyl transferases have also been used for preparing the cyclodextrins G6 and G8 from starch (Kitahata, S., Okada, S., Agric. Biol. Chem., 38, 12, 2413–2417, 1974).

These examples demonstrate the high substrate specificity toward glucosyl acceptors of glycosyl transferase enzymes expressed by *Bacillus megaterium*. Given this specificity, reactions toward substrates or metabolites having a different, complex molecular structure such as colchicones are entirely unexpected. In fact, no examples of the use of these microorganisms for the enzyme conversion of colchicone compounds to 3-glycosyl derivatives are known.

Now, it has been found that strains of *Bacillus megaterium* capable of growing in the presence of high concentrations of colchicone ($R_1$=—$OCH_3$, $R_2$=—$OCH_3$ in formula I below), 3-demethylcolchicone, or thio derivatives thereof, have exceedingly high, very specific activities for biotransforming such substrate compounds into derivative compounds, which are glycosydated exclusively at C-3 of the aromatic ring. The transformation takes place in very short times and is characterized by surprisingly high yields.

SUMMARY OF THE INVENTION

One aspect of the present invention relates to a process for the preparation of a compound of formula (I)

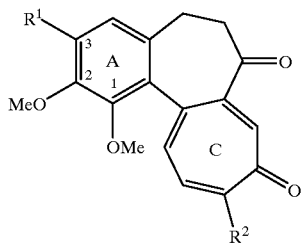

which process comprises contacting a compound of formula (II)

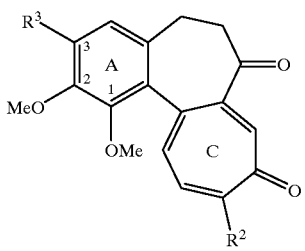

with *Bacillus megaterium* or a mutant thereof or an enzyme isolated from *Bacillus megaterium* or a mutant thereof, under conditions sufficient to effect a biotransformation of the formula II compound to the formula I compound, wherein $R_1$ is a glycoside residue, $R_2$ is $C_1$–$C_6$ alkoxy or $C_1$–$C_6$ thioalkyl, and $R_3$ is OH or methoxy. The process further comprises recovering the compound of formula (I).

In a preferred embodiment, $R_1$ is an O-glucoside residue. Preferably, the compound of formula II is glycosylated exclusively at the C-3 position of aromatic ring A to obtain a 3-O-glycosylcolchicone compound.

In one embodiment, the process of the present invention comprises culturing the *Bacillus megaterium* in a medium comprising the compound of formula II in an amount sufficient to provide a recoverable amount of the compound of formula I, preferably from about 0.1 to 3 g/l. The medium may comprise water.

The *Bacillus megaterium* strain used in the process of the invention may be selected for the ability to grow in contact with the compound of formula II in an amount sufficient to produce recoverable amounts of the compound of formula I.

The medium may comprise at least one organic nitrogen source, which is preferably selected from the group consisting of meat extract, peptone, tryptone, casein hydrolysates, or corn-step water. In another embodiment, the medium comprises at least one carbon source, which is preferably selected from the group consisting of glucose, fructose, or glycerol. In yet another embodiment, the medium comprises at least one inorganic salt selected, which is preferably selected from the group consisting of $K^+$, $Na^+$, $Mg^{++}$, or $NH_4^+$. The pH of the medium of the present invention is preferably from about 5 to 8, more preferably from about 6 to 7.

The culturing step is preferably carried out at a temperature ranging from about 20 to 45° C., more preferably from about 28 to 40° C. The culturing step is preferably, carried out at a maximum aeration level from about 1 to 2 liters of air per liter of culture per minute (vvm), more preferably from 1.5 to 2 vvm.

DETAILED DESCRIPTION OF THE PREFERRED EMBODIMENT

The compounds obtained by the biotechnological process of the invention, particularly thiocolchicosone (3-O-glucosylthiocolchicone, i.e., with reference to formula (I), $R_1$=—$OCH_3$e=—$SCH_3$), are active principles of remarkable pharmacological importance, mainly for the preparation of new antitumor therapeutics.

*Bacillus megaterium* is a Gram-positive spore generating bacterium with a cell diameter greater than about 1.0 μm. *Bacillus megaterium* is capable of growing aerobically on or within a number of culture media, is catalase-positive, and hydrolyzes gelatin.

Strains of *Bacillus megaterium* that are useful according to the invention grow satisfactorily and maintain their viability even in contact with high concentrations, for example, more than about 2 g/l, of colchicone and thiocolchicone substrates and their respective 3-demethyl derivatives such as, for example, wherein $R_1$ is a glycoside residue, $R_2$ is $C_1$–$C_6$ alkoxy or $C_1$–$C_6$ thioalkyl. Such ability may be evidenced, for example, by the examination of the growth and by microscope analysis. In contrast, congeneric species, such as *Bacillus cereus*, evidence difficulty in growing even at substrate concentrations of 1 g/l (absorbances of 10–15% of the control).

Considering the high yields of the present process, which range from about 70% to about 95%, the high selectivity and efficiency of the biotransformation is surprising and unusual.

Moreover, the microorganisms used in the bioconversion are capable of permanently maintaining catalytic activity, even after repeated fermentation steps. Thus, the microorganisms of the present invention may provide the regiospecific biotransformation in either fed-batch or continuous processes. Therefore, the present invention provides both high productivity and reproducible bioconversion levels.

The marked reaction regioselectivity of the present invention also assures that a desired product can be obtained in high quality, free from undesirable isomers. For example, with straightforward post-bioconversion processing, the product may be obtained in sufficient purity for use in, for example, therapeutic compositions. Preferably, the product is about 100% pure.

Further important advantages of the present process are the reduced complexity of the purification and recovery product steps, the low cost of the process, and the safety of the process.

Operative steps which are useful in the process of the present invention comprise are described generally below.

Initially, cultures of *Bacillus megaterium* capable of growing in the presence of high concentrations of a predetermined colchicone substrate are selected. Such cultures may be obtained, for example, from industrial samples or natural sources such as soil samples. Alternatively, cultures may be obtained from collection strains.

Isolates of the selected cultures are assayed for catalytic activity with respect to the biotransformation of the predetermined substrate into the corresponding 3-O-glycosyl derivative. In such a bioconversion assay, the substrate may be administered in gradually increasing concentrations. Additionally, the biotransformation yield, e.g., catalytic activity, of the selected strain toward the desired 3-O-glycosyl derivatives may be increased using a target specific selection procedure.

Parameters that enhance or optimize the biotransformation yield or catalytic activity of the selected strain or culture may be found and optimized. This step may comprise, for example, optimizing the fermentation conditions leading to optimal growth and/or conversion yields.

To provide stable homogeneous innocula for productive industrial scale applications, methods for conserving cultures having a desired catalytic activity are found and optimized.

Procedures and methods related to the above mentioned steps may then be scaled up for use in fermenter, batch, fed-batch and continuous processes.

Subsequent steps relate to determining and optimizing methods for post-biotransformation processing for the recovery of the transformed substrate.

At any point in the process, the selected strains may be characterized with respect to microbial properties as understood in the art.

Microorganisms usable in the present invention can be selected starting from collection cultures obtained from strain deposit centers, from soil samples of various origin, or preselected industrial strains. Selective recovery of the microorganisms may be accomplished on agar media comprising an organic nitrogen source such as, for example, peptones, yeast extracts, meat extracts, asparagine, or combination thereof, and a carbon source, such as, for example, glycerin, starch, maltose, glucose, or combination thereof. The media may have a pH from about 5 to 8, preferably from about 6 to 7. Incubation temperature range from about 20 to 45° C., preferably about 28–40° C.

As described above, colchiconic compounds may be toxic to microorganisms. The ability of a culture to grow in contact with or in the presence of a colchiconic substrate is evaluated by techniques such as serial dilution and plating the microorganisms in parallel on different agarized substrates, which comprise an amount of a colchiconic compound, e.g., 3-demethylthiocolchicone, which is sufficient to inhibit the growth of the majority of the microorganisms, preferably, the medium comprises from about 0.1 to 3 g/l of the colchiconic compound.

The colonies capable of growing in the presence of a substrate are withdrawn under sterile conditions and placed on different agarized media to verify the purity of the microorganisms and their homogeneity of growth.

Culture media used for conserving the culture, e.g., the microorganisms, are typical microbiological culture media. Such culture media may comprise organic nitrogen sources such as, for example, peptones, yeast extracts, tryptone, meat extracts, or combination thereof, a carbon source, such as, for example, glucose, maltose, glycerin, or combination thereof. Media further comprising other nitrogen sources or carbon sources suitable for growing or culturing microorganisms, as understood in the art, may be used in any step of the present invention. The media may also comprise other nutrients, such as ions or phosphorous, as suitable for microbial culture. The pH of the medium is from about 5 to 8, preferably about 6 to 7. The incubation temperatures range from about 20 to 45° C., preferably from about 28 to 40° C.

The selected microorganisms are then assayed for the capability of growing in submerged culture in the presence of colchiconic compounds and for the ability to transform the latter into the corresponding 3-glycosyl derivatives. Such assays were carried out in 100 ml flasks containing 20 ml of liquid medium, with different media formulations, comprising one or more organic nitrogen sources such as, for example, yeast extracts, peptones, tryptone, casein hydrolysates, meat extract, or corn-step liquor, one or more carbon sources, such as, for example, glucose, glycerol, starch, or saccharose, or sucrose, inorganic phosphorous and nitrogen sources, and inorganic salts of various ions, such as, for example, $K^+$, $Na^+$, $Mg^{++}$, $Ca^{++}$, $Fe^{++}$, $Mn^{++}$, etc.

Culture samples from each bioconversion assay, were analyzed to evaluate the production yield of 3-glycosyl derivatives, using thin layer chromatography (TLC) and high pressure liquid chromatography (HPLC).

The ability of the selected microorganism to transform colchiconic substrates into their corresponding 3-glycosyl derivatives was confirmed using bioconversion assays in flasks, on a 300 ml scale. The culture broths were the same as those used in the selection step.

Microorganisms that gave a positive response were used in tests for selecting conditions that enhance or optimize the bioconversion yield or catalytic activity. In particular, the optimized parameters included sources of carbon and organic nitrogen, mineral salts, temperature, stirring and aeration rates, pH, incubation time, innoculum ratio, subculture steps, and the time and form of addition of the substrate to be transformed.

The selected bacterial microorganisms, which are capable of effecting the biotransformation of the present invention, can grow on both solid and liquid culture media. The culture media may comprise one or more organic nitrogen sources, preferably, yeast extract, meat extract, peptone, tryptone, casein hydrolysates, corn-steep liquor or combination thereof. Carbon sources useful in the media comprise, glucose, fructose, saccharose, glycerol, malt extract, or combination thereof, preferably, glucose, fructose and glycerin. Additionally, glucose can be replaced by other sugars, such as, for example, fructose or galactose, without causing the loss of the glycosyl transferase activity.

The culture medium also comprises inorganic phosphorous sources, and ionic salts such as, for example, $K^+$, $Na^+$, $Mg^{++}$, $NH_4^+$, or combination thereof.

The selected microorganisms can grow at temperatures from about 20 to 45° C., preferably from about 28 to 40° C. The microorganisms can also grow in a medium having a pH of from about 5 to 8, preferably from about pH 6 to 7.

Under the conditions described above, the selected microorganisms are capable of transforming the colchiconic compounds into the corresponding 3-glycosyl derivatives. The transformations occur, for example, in submerged culture, in flasks incubated on a rotating shaker, with stirring from 150 to 250 rpm.

Due to the particular kinetics of the present biotransformation that are related to the growth of the microorganisms, the optimum conditions for the biotransformation and microbial growth are the identical. Therefore, culture media and conditions useful to promote good microbial growth, such as those based on the organic and inorganic components cited above, are also useful for obtaining a good biotransformation activity of the colchiconic substrates into their corresponding 3-glycosyl derivatives.

The substrate may be added to the culture in the initial fermentation step, or the substrate may be added in fractional aliquots starting at the initiation of fermentation.

In order to obtain mutants having the desired biotransformation activity, any of the culture samples described above can, optionally, be subjected to mutagenic treatments, using conventional mutagenesis techniques such as, for example, irradiation with ultraviolet light or other techniques. The resulting cultures may then be assayed for mutants or variants having a desired biotransformation activity or catalytic activity, as described above.

The biotransformation of the invention is based on an enzyme conversion, which starts during the growth exponential phase and continues with a progression parallel to that of the microbial growth. Maximum levels of converting the substrate into the corresponding 3-glycosyl derivative are reached within the first 48–72 hours, depending on the addition time of the substrate. Such conversion levels are preferably up to about 95% or higher.

The regioselectivity of the biotransformation is absolute: no 2-glycosyl derivatives have ever been found in the culture samples. The resulting products are exclusively extracellular.

The substrate to be transformed can be added to the culture in any form suitable for introducing the substrate to the microorganisms therein. For example, the substrate may be added in a solution of acetone or alcohol, in alcohol-water mixtures or solutions, or in dioxane.

The biotransformation of the invention can be scaled up to fermenter level, keeping the culture conditions unchanged, as far as the culture medium, temperature and processing times are concerned. In order to obtain sufficient growth, adequate levels of stirring and aeration are important such as, for example, aeration levels of about 1 to 2 liters of air per liter of culture per minute (vvm), preferably from about 1.5 to 2 vvm.

After separating the biomass from the liquid fraction by centrifugation and recovery of the supernatant or by microfiltration and recovery of the permeate, the products of the bioconversion can be extracted from the culture broths. The culture can also be treated with alcohols, to obtain an optimum recovery of the product.

The purification and the recovery of the biotransformation products can be carried out using chromatographic techniques such as, for example, separation on absorption resins and elution with an alcohol, preferably with methanol. The methanol or hydromethanol solutions containing the product can be further purified by extraction with lipophilic organic solvents, preferably with methylene chloride. After further treatments with mixtures of alcohols and organic solvents, the product can be obtained in a pure state by crystallization from the resulting alcohol solutions.

EXAMPLES

The following non-limiting examples disclose the invention in further detail.

Example 1

Aliquots of cultures of *Bacillus megaterium*, isolated from agriculture soil, were resuspended in 20 ml of sterile saline, and serially diluted to a 1:10,000,000 dilution factor. Various dilutions of the suspensions were plated on LB-Agar culture medium and on LB-Agar, which included final concentrations of 2 g/l thiocolchicone and 3-demethylthiocolchicone, respectively. Other constituents of the medium are shown in Table I.

The cultures were incubated at 28° C., for 3–4 days, in the dark. The colonies grown on the selective media, i.e., media comprising the colchicone compound, were isolated and purified by plating the microorganisms on non-selective media and incubating as above but for 24 hours.

Subsequently, the cultures were transferred to the same agar medium, in a test-tube, and incubated as above for 24 hours.

Aliquots of cultures, selected as described above, were used to inoculate 100 ml Erlenmeyer flasks containing 20 ml of culture medium ST, which is shown in Table I, and thiocolchicone or 3-demethylthiocolchicone in final amount of 0.4 mg/ml. The cultures were incubated overnight at 28° C., on a rotary shaker, at 200 rpm.

The biotransformation of the colchicone substrates was checked every 3 to 4 hours by analyzing aliquots of the culture broths using silica gel TLC, with an acetone:ethyl acetate:water 5:4:1 eluent system.

After the 4$^{th}$ day of incubation, aliquots of cultures having a desired catalytic activity towards biotransforming a substrate into the corresponding 3-glycosyl derivative, were recovered on plates using serial dilution, as described above. The recovered cultures were used for for the preparation of novel innocula in test-tubes. Accordingly, the biotransformation assay described above, which was performed in flasks, was repeated under the same conditions except for using final concentrations of thiocolchicone and 3-demethylthiocolchicone of 1 mg/ml. The most active single cultures, which had a substrate conversion equal to or higher than 70%, were used for the preparation of innocula in frozen cryotubes.

TABLE I

| Formulation of the culture media | | |
|---|---|---|
| 1) | LB-Agar | |
| | Triptone | 10 g/l |
| | Yeast extract | 5 g/l |
| | NaCl | 10 g/l |
| | Agar Agar | 15 g/l |
| | pH 7 | |
| | Sterilization: 121° C. × 20' | |
| 2) | Broth ST | |
| | Glucose | 20 g/l |
| | Glycerol | 10 g/l |
| | Peptone | 15 g/l |
| | Yeast extract | 5 g/l |
| | NaCl | 3 g/l |
| | NH$_4$Cl | 3 g/l |
| | K$_2$HPO$_4$ | 8 g/l |
| | KH$_2$PO$_4$ | 3 g/l |
| | MgSO$_4$ 7H$_2$O | 0.5 g/l |
| | pH 7 | |
| | Sterilization: 121° C. × 20' | |

Example 2

The procedure described in Example 1 was repeated using *Bacillus megaterium* cultures derived from the following collection strains (Deutsche Sammlung von Mikroorganismen, Braunschweig, Germany): DSM90, DSM 322, DSM 333, DSM 1667, DSM 1670, and DSM 1671.

Cultures having a desired catalytic activity were selected as in Example 1 and incubated for 4 days in a liquid culture comprising thiocolchicone in an amount of 1 mg/ml. TLC analysis determined that the transformation of the substrate into thiocolchicosone occurred with conversion yields varying from 30 to 70%.

Example 3

Aliquots of culture samples, selected as described in the above example, were used to inoculate 100 ml Erlenmeyer flasks containing 20 ml of the ST broth shown in Table I.

The broth cultures were incubated overnight at 30° C., on a rotary shaker with 200 rpm stirring. After incubation, a glycerol sterile solution was added to the cultures to a 20% final concentration. The cultures were then dispensed into 2 ml cryotubes and immediately immersed in liquid nitrogen.

After some days, 10% of the cultures were quickly thawed quickly at 37° C. Aliquots of each cryotube were used to inoculate 100 ml Erlenmeyer flasks containing 20 ml of medium ST, which were subsequently incubated overnight at 28° C. and with 200 rpm stirring to obtain precultures. After incubation, 2 ml of each preculture was transferred under sterile conditions to 20 ml of fresh medium ST, comprising 3-demethylthiocolchicone in a final amount of 1 g/l. The biotransformation was carried out and assayed using the conditions and methods described in Example 1. The analysis confirmed that the transformation of the substrate into the 3-glycosyl derivative occurred in yields of 70% and higher, as described above. Thus, this example demonstrates the catalytic stability of the frozen cultures.

Parallel controls of the broth cultures, plated on LB Agar immediately after thawing, confirm the viability, homogeneity and purity of the frozen cultures.

Example 4

Aliquots of cultures from a cryotube were thawed and used to inoculate 300 ml Erlenmeyer flasks containing 50 ml of medium ST (preculture). After incubation overnight at 30° C. with 250 rpm stirring, 5 ml of preculture were transferred into 50 ml of the same medium comprising 3-demethylthiocolchicone in a final amount of 1 g/l. The cultures were incubated for 4 days, in the same conditions as described above.

Every 4 hours, samples were taken to evaluate the growth level by measuring the absorbance of the solution at 600 nm. The thiocolchicosone production was assayed using TLC and HPLC. The sterility of the media was monitored using LB agar and a microscope was used for morphological examination.

TLC analysis was carried out as described in Example 1. For the HPLC analysis, 1 ml fractions of culture broths were centrifuged at 13,000 rpm for 2 minutes with 9 ml methanol. The amount of the 3-glucosyl derivative in the supernatant was analyzed by reverse phase HPLC, with isocratic elution, by means of an eluent system comprising water and acetonitrile in an 80:20 ratio.

The HPLC analysis proves that, after 72–96 hours, the bioconversion of substrate to thiocolchisone is substantially completed.

The final yields of the 3-glucosyl derivative obtained by the bioconversion range from 70 to 85%.

Example 5

The procedure described in Example 4 was repeated, but 3-demethylthiocolchicone was added to the cultures in two fractions: 0.25 g/l at the beginning and 0.74 g/l after 24 hours.

The growth and production responses of the cultures were similar to those obtained in Example 4, with thiocolchisone yields of about 90%.

Example 6

One liter of ST broth in an Erlenmeyer flask (innoculum) was inoculated with a culture from a cryotube. The flasks were incubated overnight a 30° C. with 250 rpm stirring. The innoculum was transferred in sterile into a 14 l fermenter, containing 9 l of sterile broth STL. Initially, an amount of 3-demethylthiocolchicone sufficient to produce a concentration of 0.25 g/l was added to the media. After 20 hours, additional 3-demethylthiocolchicone was added to obtain a concentration of 1 g/l.

Fermentation was carried out with stirring levels of up to 900 rpm and aeration levels of 1 to 1.5 vvm, depending on the culture growth.

Every 2 hours, samples from the culture broths were obtained and analyzed as follows: The optical density was measured at 600 nm; culture sterility and purity analysis was determined on LB Agar; morphology was determined by microscopic analysis using a Gram stain; and the thiocolchicosone content was determined by TLC and HPLC, as described in Examples 1 and 4, respectively.

After about 48 hours of fermentation, the transformation of the substrate into thiocolchisone was substantially complete with a final yield of about 85%.

Example 7

The procedure described in Example 6 was repeated with modifications, as described below. After 48 hours of fermentation, only 90% of each 10 liter culture broth was removed to obtain a first fraction from which the glycosylated product was extracted. The residual 10% of each broth was combined in the fermenter with 9 liters of fresh sterile ST medium containing 10 g of 3-demethylthiocolchicone. The fermentation was continued as described in Example 6. After 48 hours, 9 l of each culture broth was collected to obtain a second fraction and the glycosylated product was extracted. The residual volume of culture broths was combined with 9 liters of fresh sterile medium ST containing 10 g of 3-demethylthiocolchicone. The fermentation was carried out as above. After 48 hours, the final culture broth was collected to obtain a third fraction and the product extracted. The biotransformation activity of the strain remained stable within all three fractions, with conversion yields of about 80%.

Example 8

The third fraction of culture broth from the fermentation (total volume: about 27 l) was concentrated under vacuum to obtain a soft residue, which was dissolved in ethanol.

After separation by filtration, the water-ethanol fraction was concentrated to water, under vacuum, and purified by repeated extractions with methylene chloride. The aqueous fractions were concentrated and, after adjusting the pH to 10 with sodium hydroxide, extracted with chloromethylene-ethanol mixtures.

The combined organic phases were concentrated under vacuum. The resulting suspension was added with ethanol, concentrated and left to crystallize. A second crystallization with ethanol was carried out after further dissolution steps of the solid in chloromethylene-ethanol mixtures.

As various changes could be made in the above process and methods without departing from the scope of the invention, it was intended that all matter and examples contained in the above description shall be interpreted in an illustrative rather than limiting sense.

What is claimed is:

1. A process for the preparation of a compound of formula (I)

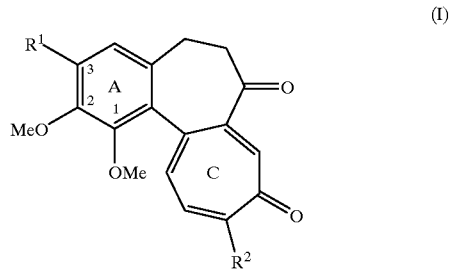

which process comprises:

contacting a compound of formula (II)

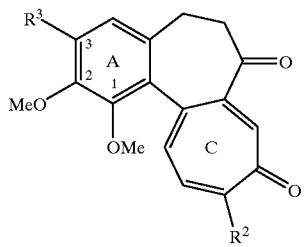

with *Bacillus megaterium,* under conditions sufficient to effect a biotransformation of the formula II compound to the formula I compound; and recovering the compound of formula (1), wherein $R_1$ is a glycoside residue, $R_2$ is $C_1$–$C_6$ alkoxy or $C_1$–$C_6$ thioalkyl, and $R_3$ is OH or methoxy.

2. The process of claim 1 wherein $R_1$ is an O-glucoside residue.

3. The process according to claim 1 wherein the compound of formula II is glycosylated exclusively at the C-3 position of aromatic ring A to obtain a 3-O-glycosylcolchicone compound.

4. The process of claim 1 wherein the contacting step comprises culturing the *Bacillus megaterium* in a medium comprising the compound of formula II in a amount sufficient to provide a recoverable amount of the compound of formula I.

5. The process of claim 4 wherein the culture medium comprises the compound of formula II in an amount from about 0.1 to 3 g/l.

6. The process of claim 1 comprising using a *Bacillus megaterium* strain selected for the ability to grow in contact with the compound of formula II in an amount sufficient to produce recoverable amounts of the compound of formula I.

7. The process according to claim 4 wherein the medium comprises water.

8. The process according to claim 4, wherein the medium comprises at least one organic nitrogen source.

9. The process according to claim 8, wherein the organic nitrogen source is selected from the group consisting of meat extract, peptone, tryptone, casein hydrolysates, or corn-step water.

10. The process according to claim 4, wherein the medium comprises at least one carbon source.

11. The process according to claim 10, wherein the carbon source is selected from the group consisting of glucose, fructose, or glycerol.

12. The process according to claim 4, wherein the medium comprises at least one inorganic salt selected from the group consisting of $K^+$, $N^+$, $Mg^{++}$, or $NH_4^+$.

13. The process according to claim 4, wherein in the pH of the medium is from about 5 to 8.

14. The process according to claim 13, wherein the pH ranges from about 6 to 7.

15. The process according to claim 4, wherein the culturing step is carried out at a temperature ranging from about 20 to 45° C.

16. The process according to claim 15, wherein the temperature ranges from about 28 to 40° C.

17. The process according to claim 1, wherein the culturing step is carried out at a maximum aeration level from about 1 to 2 liters of air per liter of culture per minute.

18. The process according to claim 17 wherein the aeration level ranges from about 1.5 to 2 vvm.

* * * * *